US00PP27917P2

(12) United States Plant Patent
Geerlings Lommerse

(10) Patent No.: US PP27,917 P2
(45) Date of Patent: Apr. 18, 2017

(54) ***ASTRANTIA* PLANT NAMED 'CAPRI'**

(50) Latin Name: *Astrantia major*
Varietal Denomination: Capri

(71) Applicant: Petronella Maria Geerlings Lommerse, Lisserbroek (NL)

(72) Inventor: Petronella Maria Geerlings Lommerse, Lisserbroek (NL)

(73) Assignee: Green Elite Collection B.V., Lisserbroek (NL)

( * ) Notice: Subject to any disclaimer, the term of this patent is extended or adjusted under 35 U.S.C. 154(b) by 0 days.

(21) Appl. No.: 14/757,311

(22) Filed: Dec. 15, 2015

(51) Int. Cl.
*A01H 5/02* (2006.01)

(52) U.S. Cl.
USPC ..... Plt./408

(58) Field of Classification Search
USPC ..... Plt./408
See application file for complete search history.

*Primary Examiner* — Annette Para
(74) *Attorney, Agent, or Firm* — C. A. Whealy

(57) ABSTRACT

A new and distinct cultivar of *Astrantia* plant named 'Capri', characterized by its upright plant habit with long flowering stems; freely-branching habit; freely and continuous flowering habit; long flowering period; relatively large flowers with showy involucral bracts that are red purple in color; and good garden performance.

3 Drawing Sheets

Botanical designation: *Astrantia major.*
Cultivar denomination: 'CAPRI'.

BACKGROUND OF THE INVENTION

The present invention relates to a new and distinct *Astrantia* plant, botanically known as *Astrantia major* and hereinafter referred to by the name 'Capri'.

The new *Astrantia* plant is a product of a planned breeding program conducted by the Inventor in Lisserbroek, The Netherlands. The objective of the breeding program is to create new freely branching *Astrantia* plants with large and attractive flowers.

The new *Astrantia* plant is a naturally-occurring whole plant mutation of *Astrantia major* 'Midnight Owl', not patented. The new *Astrantia* plant was discovered and selected by the Inventor as a single flowering plant from within a population of plants of 'Midnight Owl' in a controlled greenhouse environment in Lisserbroek, The Netherlands.

Asexual reproduction of the new *Astrantia* plant by tissue culture in Rijswijk, The Netherlands since February, 2013 has shown that the unique features of this new *Astrantia* plant are stable and reproduced true to type in successive generations.

SUMMARY OF THE INVENTION

Plants of the new *Astrantia* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Capri'. These characteristics in combination distinguish 'Capri' as a new and distinct *Astrantia* plant:

1. Upright plant habit with long flowering stems.
2. Freely-branching habit.
3. Freely and continuous flowering habit; long flowering period.
4. Relatively large flowers with showy involucral bracts that are red purple in color.
5. Good garden performance.

Plants of the new *Astrantia* differ from plants of the parent, 'Midnight Owl', primarily in the involucral bract color as plants of 'Midnight Owl' have flowers with darker red purple-colored involucral bracts.

Plants of the new *Astrantia* can be compared to plants of *Astrantia major* 'Roma', disclosed in U.S. Plant Pat. No. 11,470. In side-by-side comparisons conducted by the Inventor in Lisserbroek, The Netherlands, plants of the new *Astrantia* differ primarily from plants of 'Roma' in the following characteristics:

1. Plants of the new *Astrantia* have larger inflorescences than plants of 'Roma'.
2. Plants of the new *Astrantia* have larger flowers than plants of 'Roma'.
3. Plants of the new *Astrantia* and 'Roma' differ in involucral bract color as plants of 'Roma' have flowers with white to light pink-colored involucral bracts.

Plants of the new *Astrantia* can be compared to plants of *Astrantia major* 'Venice', disclosed in U.S. Plant Pat. No. 18,420. In side-by-side comparisons conducted by the Inventor in Lisserbroek, The Netherlands, plants of the new *Astrantia* differ primarily from plants of 'Venice' in the following characteristics:

1. Plants of the new *Astrantia* have larger inflorescences than plants of 'Venice'.
2. Plants of the new *Astrantia* and 'Venice' differ in involucral bract color as plants of 'Venice' have flowers with darker red purple-colored involucral bracts.

BRIEF DESCRIPTION OF THE PHOTOGRAPHS

The accompanying colored photographs illustrate the overall appearance of the new *Astrantia* plant showing the colors as true as it is reasonably possible to obtain in colored reproductions of this type. Colors in the photographs may differ slightly from the color values cited in the detailed botanical description which accurately describe the actual colors of the new *Astrantia* plant.

The photograph on the first sheet is a side perspective view of a typical flowering plant of 'Capri' grown in a container.

The photograph on the second sheet is a close-up view of a typical basal leaf of 'Capri'.

The photograph on the third sheet is a close-up view of typical flowering stems of 'Capri'.

DETAILED BOTANICAL DESCRIPTION

Plants used for the aforementioned photographs and the following description were grown during the summer and early autumn in an outdoor nursery in Lisserbroek, The Netherlands and under cultural practices typical of commercial *Astrantia* production. During the production of the plants, day temperatures ranged from 14° C. to 26° C. and night temperatures ranged from 5° C. to 16° C. Plants were 18 months old when the photographs and description were taken. In the following description, color references are made to The Royal Horticultural Society Colour Chart, 2015 Edition, except where general terms of ordinary dictionary significance are used.

Botanical classification: *Astrantia major* 'Capri'.

Parentage: Naturally-occurring whole plant mutation of *Astrantia major* 'Midnight Owl', not patented.

Propagation:

- *Type*.—By tissue culture.
- *Time to initiate roots, summer*.—About ten weeks at air temperatures about 21° C.
- *Time to produce a rooted young plant, summer*.—About eight months at air temperatures about 18° C.
- *Root description*.—Fine, fibrous; typically coppery brown in color, actual color of the roots is dependent on substrate composition, water quality, fertilizer type and formulation, substrate temperature and physiological age of roots.
- *Rooting habit*.—Freely branching; dense.

Plant description:

- *Plant and growth habit*.—Upright perennial flowering plant with basal rosette of leaves; overall plant shape is a narrow inverted triangle; numerous erect basal peduncles support umbels of flowers held well above the foliar plane; moderately vigorous growth habit.
- *Plant height, soil level to top of inflorescences*.—About 62.8 cm.
- *Plant width* (*spread*).—About 42.3 cm.
- *Flowering stem description*.—Arrangement: Branching mostly basal; freely branching, numerous flowering stems developing per plant during the growing season. Length: About 60 cm. Diameter: About 4 mm. Internode length: About 15.8 cm. Strength: Strong. Aspect: Upright to 30° from vertical. Texture: Axially ribbed, glabrous. Luster: Moderately glossy. Color: Close to between 143A and 146A.

Leaf description:

- *Arrangement*.—Alternate, simple.
- *Length, basal leaves*.—About 8.3 cm.
- *Length, stem leaves*.—About 6.5 cm.
- *Width, basal leaves*.—About 10.7 cm.
- *Width, stem leaves*.—About 7.9 cm.
- *Shape*.—Palmately-lobed; lobes slightly carinate and slightly curved.
- *Apex*.—Acute.
- *Base*.—Hastate.
- *Margin*.—Biserrate; teeth are mucronate.
- *Texture, upper and lower surfaces*.—Slightly rugose, glabrous.
- *Luster, upper and lower surfaces*.—Slightly glossy.
- *Venation pattern*.—Pinnate.
- *Color*.—Developing leaves, upper and lower surfaces: Close to 144A. Fully expanded leaves, upper surface: Close to NN137A; venation, close to 144A. Fully expanded leaves, lower surface: Close to between 137C and 143A; venation, close to 144B.
- *Petiole length, basal leaves*.—About 15.5 cm.
- *Petiole length, stem leaves*.—About 4.1 cm.
- *Petiole diameter, basal leaves*.—About 2.5 mm to 3 mm.
- *Petiole diameter, stem leaves*.—About 7 mm.
- *Petiole color, basal leaves, upper and lower surfaces*.—Close to between 144A and 146A.
- *Petiole color, stem leaves, upper and lower surfaces*.—Close to 143B and 144B.

Inflorescence description:

- *Flower arrangement and appearance*.—Numerous, single, minute campanulate flowers subtended by showy involucral bracts; flowers arrange in compound umbels; flowers face mostly upright to somewhat outwardly; freely flowering habit with typically about 80 flowers developing per umbel, about 18 inflorescences per compound umbel, and about 5,500 flowers developing per plant during the flowering season.
- *Natural flowering season*.—Long flowering season, flowering continuous from late spring to late summer in The Netherlands; plants begin flowering about nine months after planting.
- *Flower longevity on the plant*.—About twelve days; flowers not persistent.
- *Flower longevity as a cut flower*.—About ten days; flowers not persistent.
- *Fragrance*.—Moderate; not pleasant.
- *Flower buds*.—Length: About 2 mm. Diameter: About 1.5 mm. Shape: Obovate with flattened apex. Color: Close to 64B; towards the base, close to 143B and 147A.
- *Inflorescence height*.—About 2.5 cm.
- *Inflorescence diameter*.—About 3.7 cm.
- *Flower diameter*.—About 3 mm.
- *Flower depth* (*height*).—About 3 mm to 9 mm.
- *Petals*.—Arrangement: Five in a single whorl. Length: About 3 mm. Width: About 0.5 mm. Shape: Narrowly elliptic; recurved. Apex: Narrowly acute. Margin: Entire. Texture, upper and lower surfaces: Smooth, glabrous. Luster, upper and lower surfaces: Matte. Color: When opening, upper and lower surfaces: Close to 64A; towards the base and apex, close to N155A. Fully opened, upper and lower surfaces: Close to 64A; towards the base and apex, close to N155A.
- *Sepals*.—Arrangement: Five in a single whorl. Length: About 2 mm. Width: About 0.8 mm. Shape: Narrowly ovate. Apex: Narrowly acute. Base: Cuneate. Margin: Entire. Texture, upper and lower surfaces:

Smooth, glabrous. Color: When opening and fully opened, upper surface: Close to 146A; towards the apex, close to 71A.

When opening and fully opened, lower surface: Close to 146A; towards the apex, close to 71B to 71C.

*Involucral bracts*.—Arrangement: About 18 in a single whorl. Length: About 1.8 cm. Width: About 5 mm. Shape: Oblanceolate. Apex: Acute. Base: Attenuate. Margin: Entire. Texture, upper and lower surfaces: Smooth, glabrous. Luster, upper and lower surfaces: Matte. Color: When opening and fully opened, upper surface: Close to 60C; towards the apex, close to N186C to darker than N186C. When opening and fully opened, lower surface: Close to 60C; venation, close to 147A to darker than 147A.

*Peduncles*.—Length: About 7.4 cm. Diameter: About 2.5 mm. Strength: Strong. Aspect: Primary umbels, upright; secondary umbels, about 30° from vertical. Texture: Smooth, glabrous. Color: Close to between 143A and 146A.

*Pedicels*.—Length: About 6 mm to 9 mm. Diameter: About 0.2 mm. Strength: Strong. Aspect: Center flowers, upright; outer flowers, about 80° from vertical. Texture: Smooth, glabrous. Color: Close to 64D.

*Reproductive organs*.—Stamens: Quantity per flower: Five. Filament length: About 3 mm. Filament color: Close to 64A; towards the base, fading to close to NN155B. Anther shape: Double reniform. Anther length: About 0.8 mm. Anther color: Close to 154D. Pollen amount: Scarce. Pollen color: Close to 156D. Pistils: Quantity per flower: Two. Pistil length: About 3.75 mm. Stigma shape: Club-shaped. Stigma color: Close to 64A. Style length: About 3.5 mm. Style color: Close to 64A; towards the base, fading to close to NN155B. Ovary color: Close to 143A; ribs, close to 157B to 157C strongly tinged with close to 70A to 70B.

*Seeds and fruits*.—Seed and fruit production has not been observed on plants of the new *Astrantia*.

Disease & pest resistance: Plants of the new *Astrantia* have not been noted to be resistant to pathogens and pests common to *Astrantia* plants.

Garden performance: Plants of the new *Astrantia* have exhibited good tolerance to rain, wind and high temperatures about 30° C. and to be hardy to USDA Hardiness Zone 6.

It is claimed:

1. A new and distinct *Astrantia* plant named 'Capri' as illustrated and described.

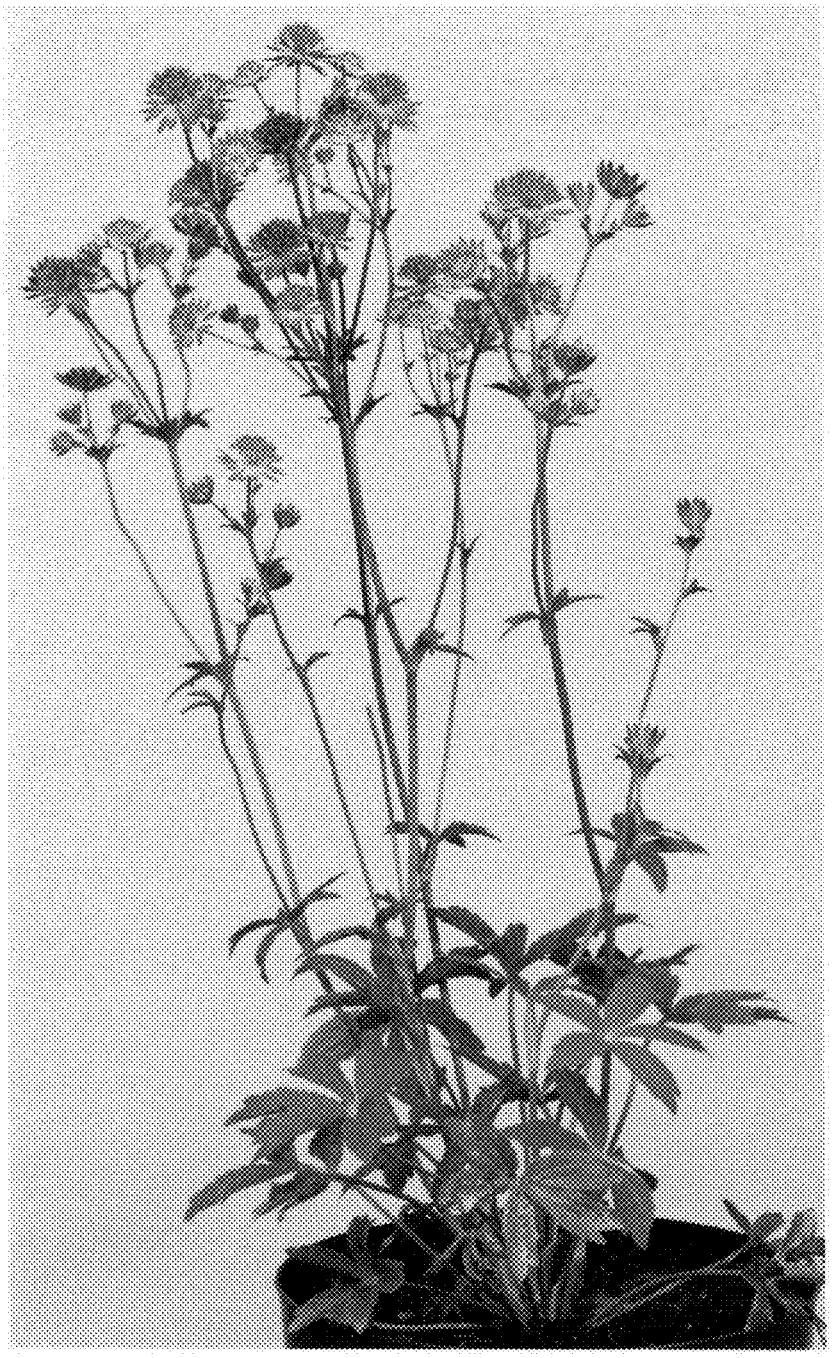

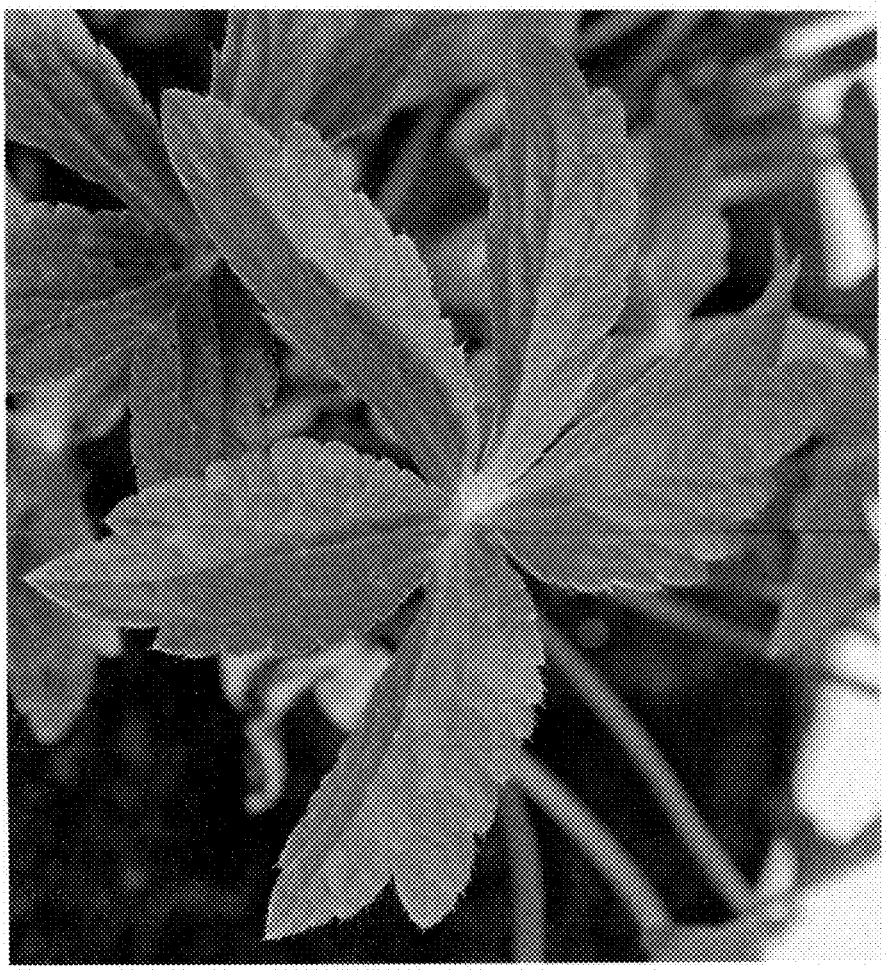

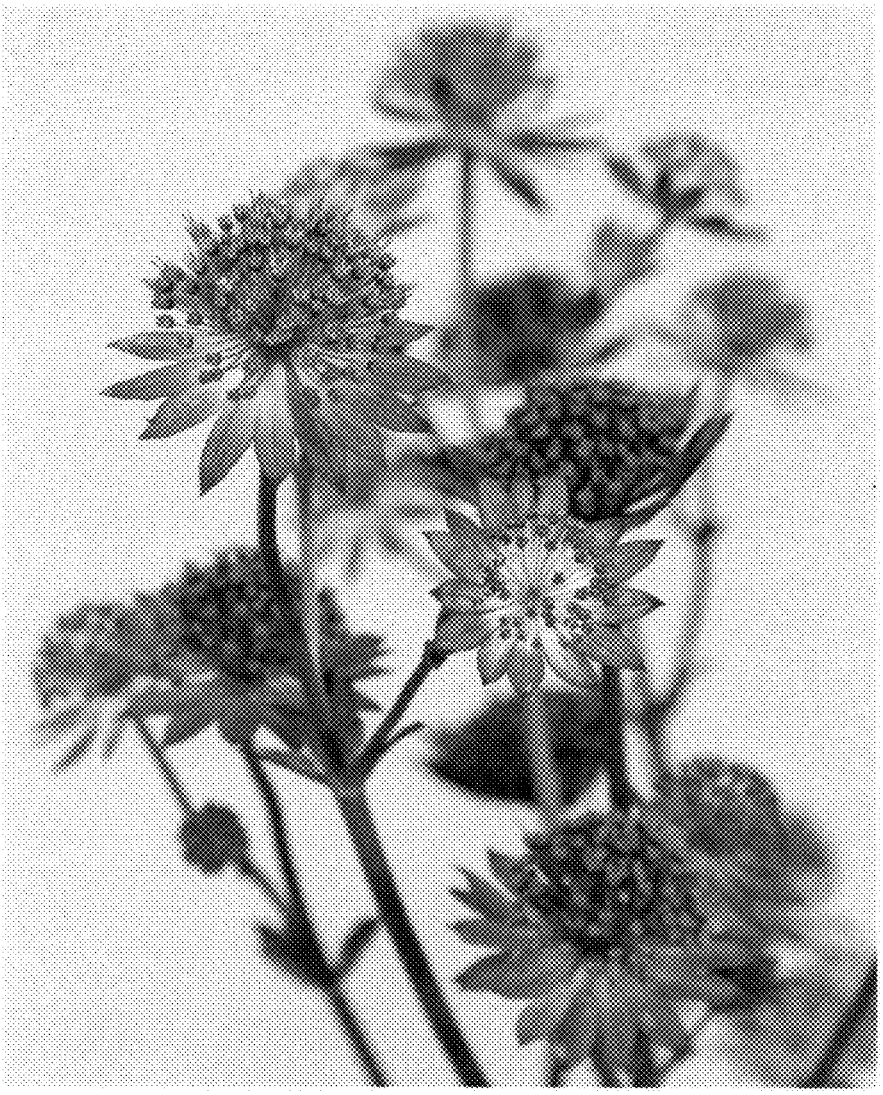

* * * * *